United States Patent [19]

McLaughlin

[11] 4,103,540

[45] Aug. 1, 1978

[54] TESTING DEVICE FOR IN-SITE CEMENTITIOUS MATERIAL

[76] Inventor: Robert R. McLaughlin, Jl. Baranangsiang, Bogor, Indonesia

[21] Appl. No.: 835,997

[22] Filed: Sep. 23, 1977

[51] Int. Cl.² .............................................. G01N 3/00
[52] U.S. Cl. .................................................... 73/88 C
[58] Field of Search ............... 73/88 C, 88 F; 52/125, 52/295

[56] References Cited

U.S. PATENT DOCUMENTS

| | | | |
|---|---|---|---|
| 2,625,815 | 1/1953 | Black | 52/295 |
| 3,283,566 | 11/1966 | Firtz | 73/88 C |
| 3,500,607 | 3/1970 | Wilson | 52/295 |
| 3,595,072 | 7/1971 | Richards | 73/88 C |

*Primary Examiner*—Anthony V. Ciarlante

[57] ABSTRACT

A testing device which will provide accurate in-site strength measurement of cast cementitious material. One or more such testing devices are cast into the cementitious material at the time of manufacture or construction of a component. At such future time as it is desired to know the strength of the cementitious material in the component an external force is applied to the protruding shaft of one of the testing devices. The force is gradually increased until rupture occurs in a precisely metered portion of the cementitious material affected by the testing device. The magnitude of force required to cause rupture is proportional to the strength of the cementitious material. Tests can be made at various times to assure adequate strength of the cementitious material for mold removal, stress loading and specified ultimate capacity.

The testing devices described herein are relatively small in comparison to most cast cementitious components. The small amount of material ruptured will not affect the usefulness of the cast cementitious component concerned.

7 Claims, 6 Drawing Figures

TESTING DEVICE FOR IN-SITE CEMENTITIOUS MATERIAL

CROSS-REFERENCE TO RELATED APPLICATION

This invention is not disclosed in any co-pending application for a patent or any issued patent.

FIELD OF THE INVENTION

The strength of a cast cementitious component is affected by many factors which may vary widely. Variations in the type, quality and proportion of ingredients; variations in mixing, handling and placing procedures; and variations in curing conditions and length of time since casting are all important factors affecting strength. Ordinary concrete is a prominent example of a cementitious material subject to all the variable factors mentioned. For the purpose of discussion the particular case of concrete will be referred to, with the understanding that the principles involved are applicable to other cast cementitious materials such as mortar, grout, plaster, and mixtures with various binders such as Portland cement, aluminous cement, ferrous cement, epoxy resin, asphalt, etc.

Some of the factors which affect concrete strength are intentionally varied in the mixing and casting process in order to obtain economy of cost and ease of placement. Others, such as type of materials and curing conditions, depend to a considerable degree on location and environment. For this reason it is essential to specify certain standards which can be applied to concrete produced anywhere in order to assure proper quality. One of the most important standards specified is strength and determination of concrete strength is of primary concern.

Previous Developments

Standards of strength can be specified in many ways. In the case of concrete it is most commonly referred to as the compressive strength at a particular time after casting, usually 28 days. Other parameters may be used in certain situations. For instance, flexural strength or tensile strength may be specified, or the time referred to might be "when supporting forms are removed from the structure" or "when the product is lifted from the casting mold". For many years the nearly universal method of testing concrete for compliance with specified strength requirements has been compressive loading, to destruction, of samples molded at the time of casting the component under consideration. These samples, usually 6 inch diameter cylinders with a height of 12 inches, are pressed to failure at particular ages and the results are imputed to correspond with the concrete which was actually cast into the component.

This method of testing has been valuable in assuring such important factors as type, quality and proportion of ingredients. It has not been a reliable test of other important factors such as mixing, handling, placing and curing of concrete actually cast in a component. In order to be satisfied with this type of testing it has been necessary to adopt a philosophy based on the understanding that millions of such tests have been made and the data available from them indicate that structures built with concrete controlled in this manner generally exhibit satisfactory qualities. The method has been tolerated but in a rather conservative construction industry old rules of thumb have often outranked questionable data in decision making. To some extent this caution has been justified. For example, when deciding whether or not to remove supporting forms from a concrete floor slab it is not prudent to rely heavily on test data from concrete test samples cured under ideal conditions in a laboratory when it is known that the concrete in the structure has been subjected to less than ideal conditions.

Another long established test method for concrete strength is test coring of the completed component. In this method cylinders of concrete are cut out of the component and compressed to rupture. Some drawbacks of this method include high cost, damage to the component and non-uniformity of results due to test core irregularities. For these reasons this method is usually reserved for checking questionable concrete.

Emergence of a more dynamic construction industry has brought with it the need for more swift and reliable data pertaining to actual conditions inside concrete components. The times at which molds may be removed or components may be lifted or loaded are of critical importance to fast moving operations which must be completed in order to permit following operations on schedule. The need has been apparent and there have been developments of various testing methods whereby rebound of a hammer on the concrete surface, penetration of a projectile fired into the concrete surface and propagation of sonic waves within the concrete mass are related to concrete strength. These methods have the advantage that they are performed directly on the concrete component under consideration. They are not, however, direct strength tests. They all depend on correlation of other properties of the concrete, such as modulus of elasticity or hardness, with supposed strength. They are often used for checking concrete which is questionable or as secondary methods when test samples provide the primary test information.

Some experimental work has been done on testing of concrete by "pullout" of steel rods cast into concrete. The tests have been limited to situations in which portions of concrete, engaged by a headed rod or bolt, were pulled out of the surface. Although the results of such tests showed good correllation with compressive cylinder tests there has never been serious practical application of the method. One reason is that the type of testing device used, and the method itself, create a jagged hole in the correct surface as the sample breaks out. Another reason is that ways to facilitate inclusion of the test rods in the concrete so they will not adversely affect form work or finishing operations have not been developed. A third reason is that the previous methods have only tested the concrete near the surface. An example of this method is illustrated in U.S. Pat. No. 3,595,072 entitled Concrete Testing Means.

SUMMARY OF THIS INVENTION

My invention, described herein, has some points of similarity to "pullout" testing but is much more versatile and has less objectionable effect on concrete placement operations and surface finish. The concrete sample tested is located at any desired depth below the surface and its rupture does not affect the surface concrete. It is a means to perform direct strength tests on components cast of cementitious materials. The method is inexpensive, fast, reliable and does not adversely affect the component. The basic element of the invention comprises a precisely sharped test grip, formed between a shaft and a sheath. The test grip is cast into the component of cementitious material at the time it is produced. The shaft extends through the sheath, which prevents bonding of that portion by the cementitious material, and protrudes from the surface of the component. When it is desired to test the strength of the cementitious material in the component, a carefully controlled and measured force is applied to the protruding shaft. The amount of force causing rupture of the cementitious material below the surface affected by the grip of the testing device is proportional to the strength of the cementitious material in the component.

The basic principles which apply to the measurement of strength in this manner are relatively straightforward. In addition to the strength of the material tested the force required to cause rupture depends on the size and shape of the test grip and whether the boundaries of the cementitious material under stress are rigidly confined or free to yield. There are a number of possible configurations of the grips and accessories, each of which will promote rupture of the cementitious material in a particular way. The strength actually tested, then, will not necessarily be purely compressive. That is also the case in the existing standard "compressive" test of concrete cylinders where rupture actually occurs in a variety of shearing modes along with compression. By correlating results of a sufficient number of the two types of test on the same material it is possible to develop a calibration for each particular variation of my invention with respect to the existing standard compressive test.

The essentials for successful employment of these testing devices are proper design, consistent precision of manufacture and consistent method of use. Within the category of proper design are included such items as rigidity and strength to prevent deformation of the testing device during use, provision of yielding or rigid elements in the test grip strain areas which will promote clear cut and reproducible rupture modes; attention to details to reduce undesirable pockets of non-uniform material which might form during casting at sharp intersections; attention to prevention of fouling in parts which should allow free movement; and due regard for surface conditions which will allow placement in components with a minimum of inconvenience to casting operations or disruption of the surface. Each of these considerations is reflected in the specific embodiments described more fully hereinafter.

BRIEF DESCRIPTION OF DRAWINGS

The advantages of my invention will become more fully apparent as the description of the invention is read in conjunction with the accompanying drawings.

DETAILED DESCRIPTION OF THE INVENTION

Figure 1:
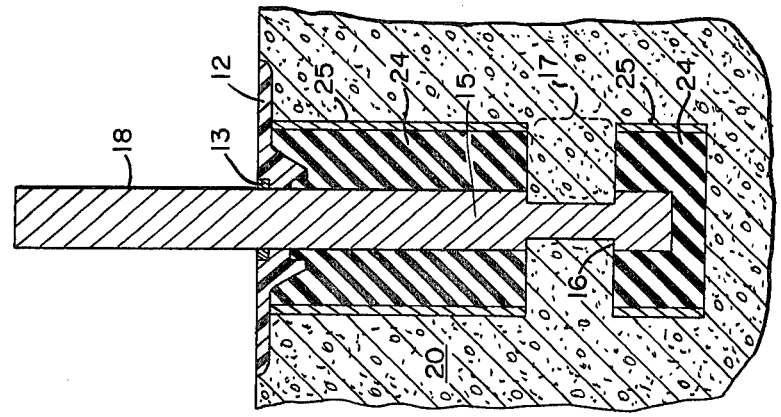
FIG. 1 is a cross-sectional view of a testing device, in one of the many possible configurations of the present invention, installed in a component of cementitious material and ready for use.

Referring now in detail to the several figures, the preferred embodiment of my invention is shown in FIG. 1 as it might be cast into a component of cementitious material. FIGS. 2, 3, 4 and 6 show some possible variations which have some of the same elements as the embodiment depicted in FIG. 1 but incorporate features affecting the installation and performance characteristics.

The particular configuration depicted in FIG. 1 comprises a sheath, 11, mounting washer, 12, grommet, 13, test anvil, 14, test rod shaft, 15, test rod pressure foot, 16, test grip, 17, test rod shank, 18, and test rod jacking coupler, 19. The testing device is shown as being cast into a cementitious material, 20, on which strength test is to be performed. Preferably, all elements have a circular cross-section perpendicular to the longitudinal axis. Sheath, 11, is of metal or plastic with sufficient rigidity to hold its shape accurately during placement and casting operations. During the testing operation test rod shaft, 15, must be able to slide freely inside sheath, 11, and any deformation of sheath, 11, might introduce error due to binding. Mounting washer, 12, is also of metal or plastic and serves two principle purposes. First, it provides the mounting means to hold the testing device in proper relationship to the component surface, whether that surface be against a mold or a free face. Second, it provides a uniform and stable surface perpendicular to the axis of the testing device which acts as the reaction bearing during test jacking. The mounting washer is designed so that it may be pried out of the cementitious material, 20, after the test and the surface can be finished as desired. Grommet, 13, is of flexible material, such as neoprene, which fits snugly in the groove between test rod shaft, 15, and mounting washer, 12. Grommet, 13, also serves two principle purposes. First, it acts as the positioning element which holds test grip, 17, in proper longitudinal conjunction with test anvil, 14. Second, it prevents cementitious material from entering the space between test rod shaft, 15, and sheath, 11, where it might cause binding. The possibility of such binding can be further reduced by application of grease in the space. Close fit of test rod shaft, 15, and sheath, 11, are desirable to limit such penetration.

Test anvil, 14, also fits closely to test rod shaft, 15, and limits penetration of cementitious material from the bottom. The primary function of test anvil, 14, however, is to provide a sharply defined boundary and solid passage reaction for test grip, 17. For that reason, test anvil, 14, is made of hard metal, preferably steel. Test rod pressure foot, 16, is the active element which applies the actual test pressure to test grip, 17. It also must be hard and sharply defined throughout the test operation. Therefore, test rod pressure foot, 16, is also made of hard metal, preferably steel.

Steel is mentioned as the preferable material because of its excellent qualities for the remainder of the test rod, that is, the test rod shaft, 15, test rod shank, 18, and test rod jacking coupler, 19. It is conceivable, however, that an even harder material may be desired for test anvil, 14, and test rod pressure foot, 16. In that case, facings or washers of such materials as silicon carbide or tungsten carbide might be bonded to the opposing faces of test anvil, 14, and test rod pressure foot, 16.

The steel used for the test rod shaft, 15, and consequently other portions of the test rod, should be a high strength type with a minimum yield strength of at least 100,000 pounds per square inch. This is within the range of many available types of steel. Surface hardness is also a factor in the selection of the test rod material as it affects test rod pressure foot, 16, and a lower limit of 400 on the Brinnell scale is considered desirable for this element.

In the preferred embodiment, test rod jacking coupler, 19, is an annular groove or notch in the upper portion of test rod shank, 18. The purpose of test rod jacking coupler, 19, is to provide a means for applying the test force to the test rod. The most satisfactory system for applying and measuring the magnitude of the force is by calibrated hydraulic jack and pressure gauge as will be described more fully in reference to FIG. 5. The annular groove or notch type coupling is quick and simple to engage and disengage from a matching chuck on the hydraulic jack. Other forms of coupling are possible, such as threads, friction grip, serated jaw pressure grip, etc.

Figure 2:
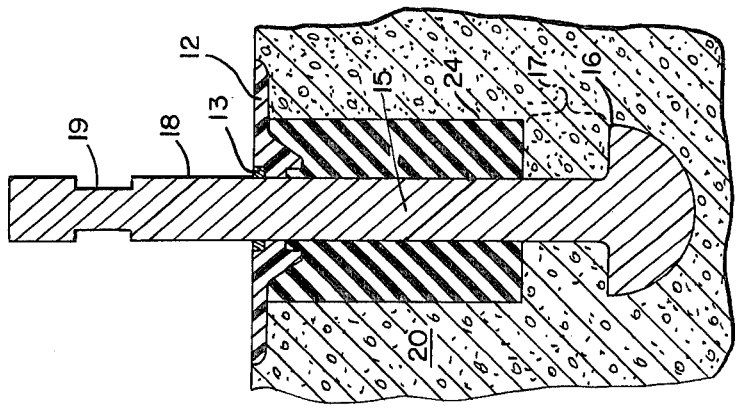
FIG. 2 is a cross-sectional view of a testing device, in another possible configuration of the present invention, installed in a component of cementitious material and which will be ready for use after the temporary plug allowing flush surface mounting has been removed and the extension shank has been attached in its place.

FIG. 2 illustrates another form of the previously described embodiment which retains many of the features disclosed in reference to FIG. 1 but which incorporates some variations affecting usability under certain conditions. Sheath, 11, mounting washer, 12, and test anvil, 14, are as previously described. Test rod shaft, 15, extends only partially through the length of sheath, 11, and the upper end is provided with a threaded female junction. Dummy shank, 22, is of metal, preferably brass, or plastic with a matching threaded male junction at its lower end. Dummy shank, 22, is installed as shown prior to placing the testing device in the cementitious component. The upper end of dummy shank, 22, is a slotted head which fits snugly in the recess of mounting washer, 12. The slotted head positions test grip, 17, in proper relation to test anvil, 14, prevents intrusion of cementitious material into the space inside sheath, 11, and provides the means for removing dummy shank, 22, after casting, by screw driver or a similar tool.

The reason for this variation from the embodiment of FIG. 1 is to allow flush surface installation of the testing device. In certain cases it may be undesirable to have protrusions through casting molds or above surfaces which must be finished by hand or machine trowelling. Another factor concerns the allowable surface conditions of the cementitious component following completion of the test. It is often specified that no ferrous metal may be left in the cementitious material less than some minimum distance from the surface. The test rod of FIG. 1 is no problem in that regard because it can be pulled through sheath, 11, and removed entirely from the component. The test rod pressure foot, 16, of FIG. 2, however, has a diameter greater than the inside of sheath, 11, and cannot easily be pulled out of the component. Therefore, provision to disconnect the test rod below the surface after testing is desirable.

In preparation for testing, dummy shank, 22, is unscrewed from test rod shaft, 15, and removed from sheath, 11. Test rod extension shank, 21, which has matching male threads on its lower end, is then screwed into the place formerly occupied by dummy shank, 22. Extension shank, 21, is of the same material as test rod shaft, 15, and has a test rod jacking coupler, 19, as previously described. Testing force is applied in the same manner as previously referred to.

The test grip, 17, shown in FIG. 2 is also a variation from that shown in FIG. 1. The particular mode of rupture of cementitious material during testing depends on the stress conditions and restraints in test grip, 17. By varying those conditions in a logical manner it is possible to produce test results which portray more accurately certain particular qualities of the cementitious material. For example, the test rod pressure foot, 16, of FIG. 1 has an outside diameter which is exactly the same as test rod shaft, 15, and just slightly smaller than the inside diameter of test anvil, 14. Test grip, 17, of FIG. 1 allows no strain relief of the cementitious material except along a cylindrical shearing surface connecting the outside face of test rod pressure foot, 16, and the inside face of test anvil, 14. In the case of FIG. 1, the test rupture mode is essentially pure shear. The arrangement of FIG. 2 causes quite different stress conditions in the cementitious material affected by test grip, 17. In this case the outside diameter of test rod pressure foot, 16, is larger than the inside diameter of test anvil, 14. Ideally, the outside diameter of test rod pressure foot, 16, is the same as the outside diameter of test anvil, 14. Application of test force upward on test rod pressure foot, 16, causes compression of the annular ring of cementitious material within test grip, 17. Rupture in the compression mode is promoted by allowing lateral strain of the annular ring of cementitious material in test grip, 17. This is accomplished by installing test rod pressure relief void, 23, in test grip, 17. Test rod pressure relief void, 23, is a sleeve of relatively compressible, impervious material such as low density neoprene, polyurethane, styrofoam or other plastic which will hold its shape accurately during the casting process of the cementitious material, 20, but which will yield freely under expansion pressure from cementitious material, 20, during compression in test grip, 17. The rupture mode under these circumstances will be compressive in the same sense as it is in the standard compressive test of concrete cylinders. In both cases "diagonal tension" can develop toward free surfaces causing rupture.

Figure 3:
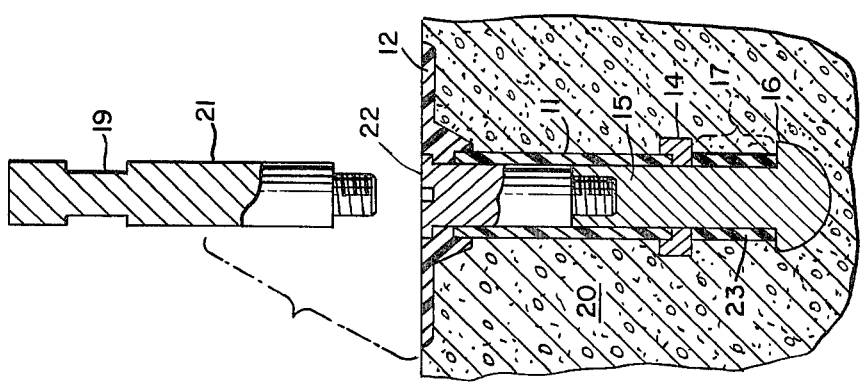
FIG. 3 is a cross-sectional view showing another possible configuration of a testing device in the present invention with sheath and test grip types which may be used as alternatives to the sheath and test grip types shown in FIGS. 1 and 2.

Unless a particular mode of rupture is provided for in the design of test grip, 17, the test results will not be consistent nor meaningful. FIG. 3 illustrates another variation of the testing device wherein sheath/pressure relief void, 24, serves the dual purpose implied by its name. Mounting washer, 12, grommet, 13, test rod shaft, 15, test rod shank, 18, and test rod jacking coupler, 19, are the same as previously described in reference to FIG. 1. Sheath/pressure relief void, 24, is made of material with the same characteristics as previously mentioned regarding test rod pressure relief void, 23. In the configuration of FIG. 3 sheath/pressure relief void, 24, allows freedom for the cementitious material, 20, in test grip, 17, to yield away from test rod pressure foot, 16. The rupture mode in this case depends on the angle of inclination of the surface connecting the outside circumference of test rod pressure foot, 16, and the outside circumference of sheath/pressure relief void, 24. In the particular configuration shown in FIG. 3 the outside diameters are the same and rupture will occur as a shearing along the cylindrical surface which connects the outer circumferences of test rod pressure foot, 16, and sheath/pressure relief void, 24.

In the case where the outside diameter of test rod pressure foot, 16, of FIG. 3 is smaller than the outside diameter of sheath/pressure relief void, 24, the rupture will occur as a combination of shear and diagonal tension on the truncated conical surface connecting their outer circumferences. The more acute the base angle of this cone, which is inverted in this case, the more pronounced will be the diagonal tension effect on the rupture mode. Base angles more acute than about 45° will not form but rather rupture of cementitious material affected by the test grip, 17, will occur on a surface intersecting sheath/pressure relief void, 24, somewhere inside its outer limits.

Figure 4:
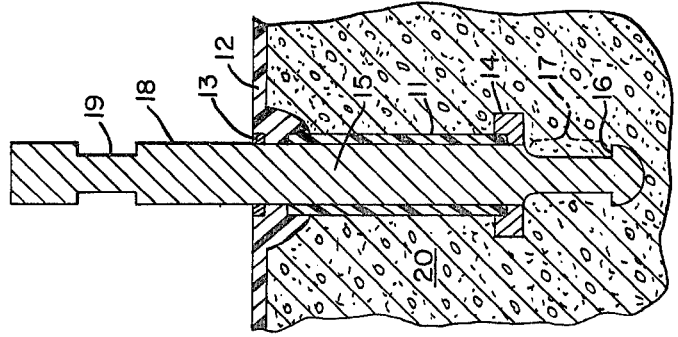
FIG. 4 is a cross-sectional view showing further variations of sheath, test grip and accessories which may be included in the present invention as alternatives to those shown in FIGS. 1, 2 and 3.

FIG. 4 shows another variation of the testing device. In this case mounting washer, 12, grommet, 13, test rod shaft, 15, test rod pressure foot, 16, and test rod shank, 18, are the same as previously described with reference to FIG. 1. Test rod shank, 18, does not have any special provision for application of a test force, such as jacking coupler, 19, of FIG. 1. A smooth test rod shank, 18, will suffice for this purpose if the jaws of the jack are of appropriate design. Sheath/pressure relief void, 24, has the same form and function above test grip, 17, as was described in reference to FIG. 3. However, in the variation of FIG. 4 it is enclosed by outer shell, 25, and forms the lower boundary of test grip, 17, as well. Outer shell, 25, is of metal or other hard material and serves as a definite boundary for the cementitious material, 20, affected by test grip, 17.

The rupture mode of cementitious material, 20, affected by test grip, 17, of FIG. 4 is similar to that described in reference to FIG. 3. Tests have shown that inclusion of outer shell, 25, and application of test force at the inner edge of test grip, 17, by the form of test rod pressure foot, 16, shown in FIG. 4 enhance the purity of the diagonal tension failure mode in case that is desirable. Another feature of this variation of the testing device is that testing can be accomplished by application of either a tensile or compressive force to test rod shank, 18, with similar results.

Figure 5:
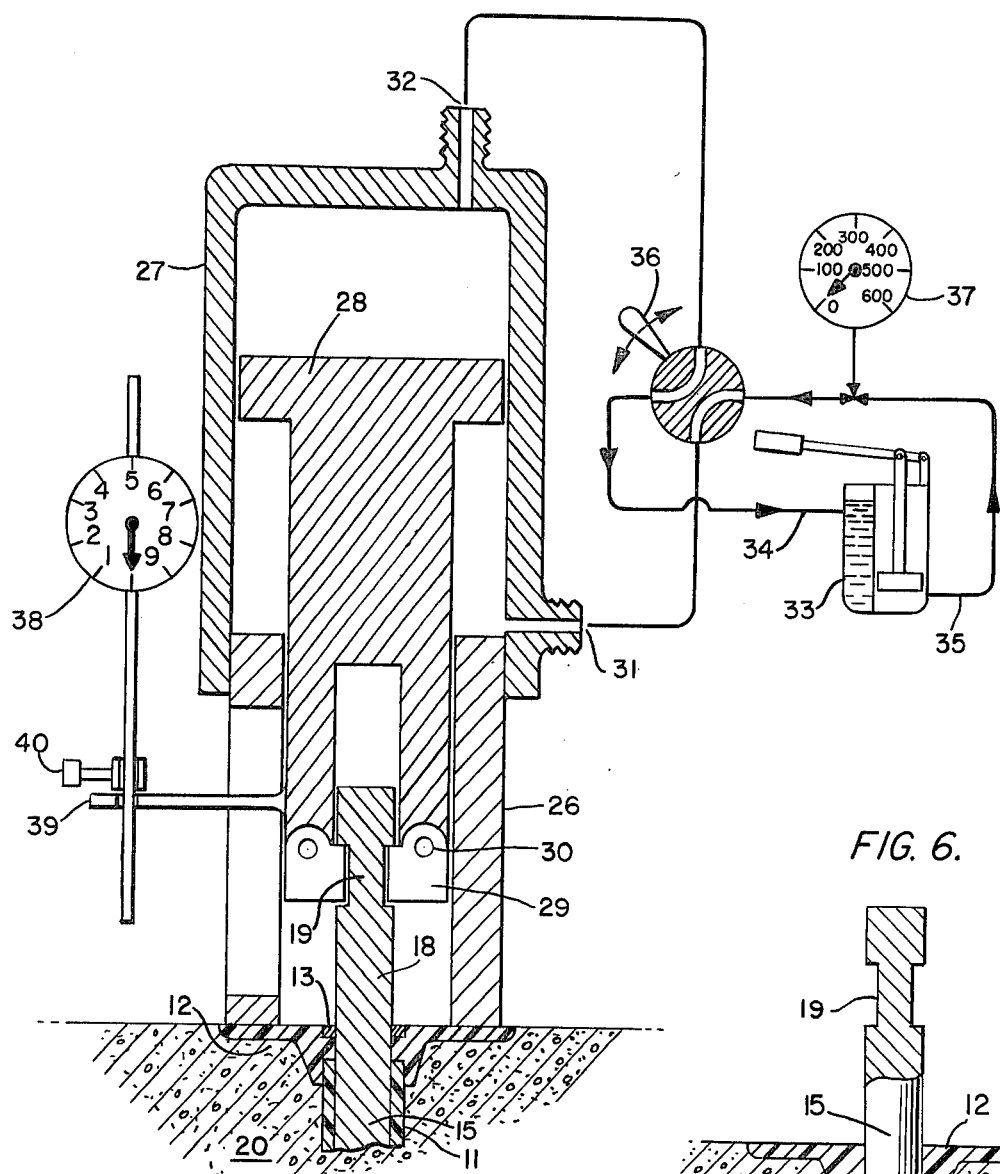
FIG. 5 is a schematic cross-sectional view of a testing device in the present invention with auxiliary equipment as it might be arranged during actual testing of a cementitious component.

FIG. 5 schematically illustrates one method of performing the test operation to determine strength of cementitious material using the testing device in the present invention. In FIG. 5 the upper portion of a testing device similar to that shown in FIG. 1 including sheath, 11, mounting washer, 12, grommet, 13, test rod shaft, 18, and test rod jacking coupler, 19, is seen embedded in cementitious material, 20. Equipment to apply the test force is shown schematically in one possible configuration including jack reaction base, 26, jack cylinder, 27, jack piston, 28, jack jaws, 29, jack jaw swivel, 30, jacking pressure port, 31, releasing pressure port, 32, hydraulic pump, 33, pump intake port, 34, pump discharge port, 35, selection valve, 36, pressure gauge, 37, strain gauge, 38, strain gauge reference arm, 39, and reference clamp, 40.

Figure 6:
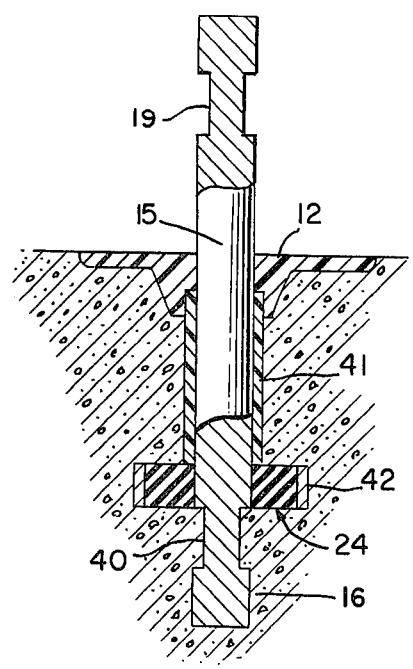
FIG. 6 is a cross-sectional view depicting a further variation of the test device shown in FIGS. 1, 2, 3 and 4.

FIG. 6 shows a further variation of the testing device. In this case test rod shaft, 15, is of constant diameter with annular grooves, 19, and 40, at the two ends. There is a mounting washer, 12, a plastic sheath, 41, and a metal ring, 42, surrounding compressible material, 24. The pressure foot, 16, is the same diameter as the test rod shaft, 15, and the annular groove, 40, defines the inner surface of the test grip. When the test rod shaft, 15, is withdrawn the reaction is entirely against the concrete in the test grip, the compressible material 24, carrying no force. Because of the easy compressibility of compressible material, 24, it is analogous to a free surface which can be located at any depth desired.

The basic jacking device depicted in FIG. 5 can be assembled from components generally available from many sources. Jack reaction base, 26, is rigidly attached to a jack cylinder, 27. Inside is jack piston, 28, which is capable of travel in either of two directions depending on whether pressurized hydraulic fluid enters through jacking pressure port, 31, or releasing pressure port, 32. Selection of the jacking device requires cognizance of size and capacity requirements for compatibility with the testing device. Jack jaws, 29, and their method of attachment, represented in this case by jack jaw swivels, 30, are variations of the basic jacking device intended specifically for use with the particular jacking coupler shown. In the embodiment illustrated in FIG. 5 jack jaws, 29, are free to rotate about jack jaw swivels, 30, when the bottom of jack piston, 28, has traveled sufficiently beyond the bottom of jack reaction base, 26, in the release direction. Under those conditions jack jaws, 29, can be mated with test rod jacking coupler, 19, and when jack piston, 28, is actuated in the jacking direction, retraction into the close-fitting space inside jack reaction base, 26, locks the jack jaws, 29, into test rod jacking coupler, 19. The material of jack jaws, 29, and jack jaw swivels, 30, should be hard, high strength steel, similar to that of test rod shaft, 15.

The auxiliary equipment for providing pressurized hydraulic fluid to the jacking device in FIG. 5 comprises a hydraulic pump, 33, with a pump intake, 34, and a pump discharge, 35. The pump is depicted schematically as a hand operated type although it could be motorized. Ordinary size test devices will require relatively light loading and short strain to rupture. Hand operated pumps are suitable but a motorized pump could also incorporate a time-strain control which would be useful. Selection valve, 36, is a two-position rotating valve which directs pressurized fluid from pump discharge, 35, to either jacking pressure port, 31, or releasing pressure port, 32. In the former position hydraulic fluid expelled through releasing pressure port, 32, is directed to pump intake, 34, and in the latter position hydraulic fluid expelled through jacking pressure port, 31, is directed to pump intake, 34.

Pressure gauge, 37, is an accurately calibrated sensitive gauge which can be graduated in terms of hydraulic pressure, jacking force applied or directly in units of cementitious material strength. The latter is restrictive to the versatility of the system since the various types and sizes of test grips will all relate different functions of rupture stress and applied force. Graduation in terms of jacking force is preferred and calibration charts relating gauge readings to the cementitious material strengths comensurate therewith for the various types and sizes of testing device are used for interpretation of results. Pressure gauge, 37, is equipped with a recording needle which registers the highest pressure attained during a particular operation. The recording needle can be reset at any time.

Strain gauge, 38, is mounted on the side of jack cylinder, 27, with its actuating rod passing through a hole in strain gauge reference arm, 39, which is attached to jack piston, 28. Relative movement between jack cylinder, 27, and jack piston, 28, can be measured when reference clamp, 40, is tightened in contact with strain gauge reference arm, 39, In practice, strain gauge, 38, is not actuated until the jacking equipment is ready for the actual application of force to the testing device. At that time reference clamp, 40, is tightened snug against the top of strain gauge reference arm, 39, while strain gauge, 38, indicates zero. Subsequent readings of strain gauge, 38, will indicate strain of the testing device under application of the testing force. In practice, pressure gauge, 37, and strain gauge, 38, will be mounted in proximity to each other to allow simultaneous viewing by the test operation. A sudden jump in strain, indicated by strain gauge, 38, accompanied by a simultaneous decrease in test force, indicated by pressure gauge, 37, signals rupture of the cemetitious material in test grip, 17. At that point the test is complete. Application of test force should be discontinued and the final pressure shown by the recording pointer of pressure gauge, 37, should be noted.

Reference to a calibration chart for the particular type and size of testing device in use, with respect to the final pressure noted from test gauge, 37, will provide accurate and consistent strength data for cementitious materials. Although the testing devices of FIGS. 1, 2, 3, 4, 5 and 6 are shown as if mounted in the vertical position it should be understood that mounting in any position is feasible. Also, depth of the test in the cementitious material can be varied by changing the lengths of sheath, 11, or sheath/pressure relief void, 24, and test rod shaft, 15.

Although the present invention has been described with reference to a particular embodiment thereof, it should be understood that those skilled in the art may make other modifications and embodiments thereof which will fall within the spirit and scope of the principles of this invention.

What is claimed as new and desired to be secured by patent of the United States is:

1. A device for testing the strength of cementitious material at some depth below the surface comprising in combination:
    (a) a test rod of generally cylindrical shape,
    (b) a reaction piece of generally cylindrical shape and having a hollow bore,
    (c) said test rod having a central portion adapted for sliding engagement within said bore,
    (d) said hollow bore having a length less than said test rod whereby each end of said rod protrudes from said bore,
    (e) said test rod having a first end comprising a head portion with means to which an external axial force may be applied,
    (f) said test rod having a second end comprising a foot portion,
    (g) said test rod having a generally cylindrical portion extending from the central portion to the foot portion and occupying a region of cementitious material comprising the test grip,
    (h) said test grip portion of said test rod having an inner diameter less than the diameter of said foot,
    (i) said foot having a generally flat surface in a plane normal to the axis of the test rod adjoining the test grip portion,
    (j) said reaction piece having a section with an outer diameter greater than said foot and a generally flat surface facing said foot, and terminating at an inner diameter adjoining said test rod whereby said device may be cast into the cementitious material at some depth with said foot and said reaction piece spaced apart the distance comprising said test grip and an axial force may be applied to determine the strength of said cementitious material as a function of the force required to rupture the cementitious material in the test grip between said foot and said reaction piece.

2. The combination of claim 1 which includes at the end of the test rod to which an axial force is applied, an indentation cooperating with a protuberance in the means to apply axial pressure.

3. The combination of claim 1 which includes a test rod composed of a plurality of detachable rods to allow a flush mounting.

4. The combination of claim 1 which includes means on the hollow sheath to mount the device flush with the surface and extending inwardly into the freshly poured cementitious material.

5. The combination of claim 1 which includes an anvil on said hollow sheath, of hard metal, having a precise reaction boundary for test grip pressure applied by said test rod.

6. The combination of claim 1 which includes compressible material surrounding a portion of the central portion of the main axis of the test rod which will yield as the test grip pressure is applied by said test rod.

7. The combination of claim 1 in which the test rod has a foot portion gripping a portion of the cementitious material beneath the surface and a hollow compressible member below and above the foot portion whereby the test rod may be pulled or pushed to measure the strength of the cementitious material.

* * * * *